(12) United States Patent
DeVore et al.

(10) Patent No.: US 7,015,013 B2
(45) Date of Patent: Mar. 21, 2006

(54) METHOD FOR LOCALIZED STAINING OF AN INTACT CORNEAL TISSUE SURFACE

(75) Inventors: Dale Paul DeVore, Chelmsford, MA (US); Braden Patrick DeVore, Las Vegas, NV (US)

(73) Assignee: 3D Vision Systems, LLC, Norwood, MA (US)

( * ) Notice: Subject to any disclaimer, the term of this patent is extended or adjusted under 35 U.S.C. 154(b) by 0 days.

(21) Appl. No.: 10/846,742

(22) Filed: May 14, 2004

(65) Prior Publication Data

US 2005/0009134 A1    Jan. 13, 2005

Related U.S. Application Data

(60) Provisional application No. 60/470,944, filed on May 15, 2003.

(51) Int. Cl.
*G01N 1/30* (2006.01)

(52) U.S. Cl. ..................... 435/40.5; 435/30

(58) Field of Classification Search .............. 128/898; 604/294, 289, 290

See application file for complete search history.

(56) References Cited

U.S. PATENT DOCUMENTS

| | | | |
|---|---|---|---|
| 5,104,957 A | 4/1992 | Kelman et al. | 527/201 |
| 5,201,764 A | 4/1993 | Kelman et al. | 623/6 |
| 5,219,895 A | 6/1993 | Kelman et al. | 522/68 |
| 5,332,809 A | 7/1994 | Della Valle et al. | 536/119 |
| 5,354,336 A | 10/1994 | Kelman et al. | 623/6 |
| 5,476,515 A | 12/1995 | Kelman et al. | 623/6 |
| 5,480,427 A | 1/1996 | Kelman et al. | 623/6 |
| 5,631,243 A | 5/1997 | Kelman et al. | 514/56 |
| 6,161,544 A | 12/2000 | DeVore et al. | 128/898 |
| 6,306,120 B1 * | 10/2001 | Tan | 604/294 |

\* cited by examiner

*Primary Examiner*—Sandy Saucier
*Assistant Examiner*—Satyendra K. Singh
(74) *Attorney, Agent, or Firm*—Barlow, Josephs & Holmes, Ltd.

(57) ABSTRACT

The present disclosure describes novel methods for localized and controlled staining of intact corneal tissue surfaces to provide therapeutic benefits in ophthalmic applications, such as for example, the correction of iris defects, the correction of corneal tissue scarring, and the creation of a pupil in aniridia. A first method for staining tissue surfaces is directed to covalently bonding sulfonic acid dyes to deprotonated proteins in tissue. Another disclosed method is directed to staining corneal tissue surfaces with black sulfonic acid dye compositions, particularly for forming black rings on the corneal surface.

16 Claims, No Drawings

METHOD FOR LOCALIZED STAINING OF AN INTACT CORNEAL TISSUE SURFACE

CLAIM OF PRIORITY

This application claims priority to U.S. Provisional Patent Application No. 60/470,944 entitled "Methods for Staining Tissue Surfaces", filed May 15, 2003.

FIELD OF THE INVENTION

The present invention relates to methods for staining tissue surfaces by covalently binding sulfonic acid dyes to deprotonated proteins in tissue. This invention also relates to methods for staining tissue surfaces with black sulfonic acid dye compositions, particularly for forming black rings on the corneal surface.

BACKGROUND

Common methods of applying permanent or semi-permanent color to tissue include tattooing and application of inks. Corneal tattooing has been used to provide Cosmesis for iris defects and to create a pupil in aniridia. These techniques involve the implantation of tattoo pigments into the corneal lamellae. In skin tattoos, pigments are injected just below the epidermis and just above the papillary dermis using special needles. Inks, particularly India inks, are traditionally used to mark tissues prior to surgical procedures. Alternative methods to mark tissue surfaces use alcian blue, artist's pigments, and typist's correction fluid. None of these marking modalities are used for therapeutic benefit.

Many chemical dyes are in the form of sulfonic acids. Sulfonic acids, anhydrides, sulfonyl chlorides, and acid chlorides are classes of chemical compounds that react with free amines of proteins resulting in the covalent attachment of the specific chemical moieties to proteins. These compounds are commonly known as acylation reagents. Acylation of amino groups in proteins has been widely used ("Chemical Reagents for Protein Modification", $2^{nd}$. Edition, Ed. Roger L. Lundblad, CRC Press, Boca Raton, 1991). Such reactions have been used to introduce structural probes into proteins at specific sites to modify lysyl residues. Acylation reactions have been used to derivatize soluble and insoluble collagen and have been described by DeVore, et.al. in series of patents (U.S. Pat. Nos. 4,713,446, 4,851,513, 4,969,912, 5,067,961, 5,104,957, 5,201,764, 5,219,895, 5,332,809, 5,354,336, 5,476,515, 5,480,427, 5,631,243, and 6,161,544). However, none of these patents describe the use of acylation to stain or dye surfaces or sections of intact tissue.

The present invention describes methods for localized and controlled staining of intact tissue surfaces to provide therapeutic benefit in ophthalmic applications.

SUMMARY OF INVENTION

The present invention features a method for applying a stain (or dye) to tissue surfaces for therapeutic and cosmesis applications. The method includes steps of (1) applying a treatment device to the tissue surface such that the desired area of the tissue surface is exposed to treatment solutions; (2) pretreating the exposed tissue surface with slightly alkaline buffer solution for 1–2 minutes to bring the pH of the tissue surface to between 7.5 and 9.5 resulting in deprotonation of $\epsilon$-amino groups of lysine residues on exposed proteins; (3) removing the pretreatment buffer solution using an absorbent sponge; (4) applying the chemical dye or stain (acylating agent at a concentration of between 0.1 mg/mL and 100 mg/mL, preferably between 1 mg/mL and 50 mg/mL, in the same slightly alkaline buffer used in the pretreatment solution) to the exposed area such that the chemical dye or stain immediately reacts with the exposed, pretreated tissue surface resulting in covalent bonding of the pendant chemical dye or stain to the deprotonated $\epsilon$-amino groups of lysine residues on exposed proteins; (5) thorough rinsing of the total tissue surface to remove unreacted chemical stain or dye leaving a superficial stain or dye in the desired treatment area. The predominant protein to react with the sulfonic acid dye is collagen.

The tissues to be treated include skin, cornea, scleral tissue, or conjunctival tissue. The preferred tissue surface is that of the human cornea. The preferred chemical dyes include the following sulfonic acid reagents imparting a dark, blue-black stain, C.I. 14645 Eriochrome Black T, C.I. 26370 Acid Black 24; C.I. 65005 Acid Black 48; C.I. 20470 Naphthol Blue Black; and Reactive Black 5. The most preferred black sulfonic acid dye is Reactive Black 5.

The application of black stains to the corneal surface has the following cosmesis and therapeutic applications: to cover white or gray corneal scars, to create a pupil in aniridia, to cover large iridectomy; to form a corneal ring to control light rays striking the macular, to improve depth of focus in treatment of refractive errors, and to restrict light scatter in corneal opacities. Several US patents describe the masked or tinted lenses or annular masked lenses for treatment of optical aberrations. These include U.S. Pat. Nos. 4,955,904; 5,662,706; 5,757,458; 5,786,883; and 5,965,330. However, none describe the application of a stain or dye mask or tint applied directly to corneal tissue.

DEFINITIONS

By "acylating agent" is meant an agent that transfers an acyl group to another nucleophile. Examples of acylation agents are sulfonic acids, anhydrides, sulfonyl chlorides, and acid chlorides. The black dyes and other color dyes used in this invention are primarily in the form of sulfonic acids.

Dyes or stains are agents that impart color to exposed surfaces. A listing of sulfonic acid stains and dyes can be found in the Sigma-Aldrich Chemical company catalogue.

Superficial surface is meant to be the very top layer of tissues, to depths of about 2 to 50 microns.

DETAILED DESCRIPTION

The present invention provides methods for staining the superficial layer of exposed tissue surfaces for therapeutic and cosmesis purposes. Staining is accomplished by exposing pretreated tissue surfaces to sulfonic acid dyes such that the dye binds covalently to deprotonated $\epsilon$-amino groups of lysine residues on exposed proteins, predominantly collagen.

The present invention provides methods for staining the superficial layer of exposed tissue surfaces of skin, cornea, sclera, conjunctiva and other tissues. The invention primarily provides methods for controlled, superficial staining of the corneal tissue. Staining maybe accomplished on the corneal surface or on exposed corneal lamellae.

In general, the acylating agent may include dyes in the form of sulfonic acids, anhydrides, sulfonyl chlorides, and acid chlorides. Most dye acylating agents are sulfonic acids. Concentrations of the dye chemical range from 0.1 mg/mL to 100 mg/mL, preferably from 1 mg/mL to 50 mg/mL.

Prior to addition of the dye reagent, the tissue is pretreated with a solution exhibiting a pH from 7.5–9.5. The solution may be composed of a single component, such as disodium phosphate or sodium pyrophosphate or sodium borate, or may be a buffer composition providing a pH ranging from 7.5–9.5. The concentration of the alkaline solution ranges from 0.01M to 0.2M.

The device for applying the sulfonic acid dye or stain to the corneal surface is composed of a series of concentric circles. The center of the concentric circles is solid and is seated on the corneal apex, preventing exposure of the central cornea to the sulfonic acid dye or stain. An intermediate concentric circle is open to the surface of the cornea allowing exposure of this surface to the sulfonic acid dye or stain. The outer circle is also solid and seated firmly on the corneal surface preventing exposure of the corneal surface to the sulfonic acid dye or stain. The width of the intermediate concentric circle can be adjusted to allow exposure of the corneal surface to predetermined widths of sulfonic acid dye or stain. Thus, a ring of predetermined width can be formed on the corneal surface for specific therapeutic applications. In one design, a port is fabricated fitting the end of a 1.0–2.5 cc syringe. Dye or stain solution is injected into the open ring through this delivery port to treat the exposed tissue surface. The dye or strain is also removed using this port and rinse solutions applied to remove unbound dye or stain. The extent of tissue staining is dependent on the concentration of the dye or stain, exposure time, and the pH of the exposed tissue. Other configurations for delivery devices can be fabricated to stain or dye predetermined regions of the cornea surface for Cosmesis. For example, a dry sponge, pre-dosed with an appropriate amount of black stain or dye is fabricated to specific dimensions such that when the dry, pre-dosed sponge is wet, the dye is delivered to the exposed tissue surface. The dry, pre-dosed sponge is fabricated in the form of a thin ring. The ring is then placed in a delivery device. Fluid is then applied to the ring causing it to wet and instantly deliver the pre-dosed dye or stain to the exposed tissue surface to form a black ring in the same dimensions as the delivery ring. The delivery ring may be fabricated in different dimensions, thickness and diameter to apply the desired stain dimensions.

The features and other details of the invention will now be more particularly described and pointed out in the following examples describing preferred techniques and experimental results. These examples are provided for the purpose of illustrating the invention and should not be construed as limiting

EXAMPLES

Staining or Dying Human Dermal Tissue

Outdated, lyophilized human dermis (Dermaplant, Collagenesis, Inc.) was rehydrated in sterile water for 15 minutes and then placed in a bath containing sterile 0.2M disodium phosphate solution for 2 minutes. The wet tissue was dried with Kimwipes and placed in a bath containing a sterile solution of Reactive Black 5 dissolved in 0.2M disodium phosphate solution. After 1 minute the tissue was removed from the dye solution and thoroughly rinsed with 0.1M phosphate buffer, pH 7.2 until dye no longer eluted from the tissue. The resultant tissue stained very deep blue-black. This simple experiment demonstrated the attachment of Reactive Black 5 to intact tissue.

Lyophilized human dermis was rehydrated in sterile water and wiped dry with Kimwipes. A crude device composed of concentric circles, as described above, was placed firmly on the surface of the tissue and held in place with small clamps. The exposed concentric ring was flushes with alkaline solution, 0.2M disodium phosphate, pH 9.0. After 2 minutes, the solution was removed using a pipette. A solution of Reactive Black 5 (50 mg/mL) in 0.2M disodium phosphate, pH 9.0, was applied to the exposed surface and allowed to react for 2 minutes. This solution was removed using a pipette. A solution of 0.1M phosphate buffer, pH 7.2 was added to concentric ring to flush dilute the residual Reactive Black 5 solution. This was repeated 3 times such that the solution remained clear and colorless indicating that residual Reactive Black 5 has been thoroughly flushes. The treatment device was removed and the entire tissue washed with 0.1M phosphate buffer, pH 7.2. The result of this treatment was the formation of a thin deep blue-black ring, approximately 1.5 mm wide on the dermal tissue surface. Minimal bleeding into unexposed tissue was observed.

A preserved cat eye, with intact cornea, vitreous and scleral tissue, was removed from the preservation solution and placed in a bath of 0.2M disodium phosphate, pH 9.2, for 2 minutes. The eye was then removed from the bath and placed in a holding device allowing the cornea to be exposed for treatment. Reactive Black 5 dissolved in 0.2M disodium phosphate, pH 9.2, was applied to the entire exposed surface of the cat cornea. After 1 minute, the cornea was thoroughly washed with 0.1M phosphate buffer, pH 7.2, to remove unbound dye. The cornea surface appeared faintly blue-black. Dye solution that leaked onto the scleral ring surrounding the eye appeared deep blue-black. A thin ring was etched into the corneal surface using a scalpel blade. Reactive Black 5 solution was again applied to the corneal surface. After 1 minute, the cornea was thoroughly washed with 0.1M phosphate buffer, pH 7.2 until the wash solution appeared clear and colorless. A thin ring of deep blue-black color was observed on the corneal surface. This experiment clearly demonstrated the formation of a deep blue-black ring on the corneal surface of a preserved cat eye. Similar techniques will be useful for cosmesis to cover corneal scars or to create a pupil in aniridia. In addition, a corneal ring can be formed on the corneal surface to improve depth of focus for certain refractive errors and to restrict light scatter in certain corneal opacities. Furthermore, a similar corneal ring has potential applications in restricting orientation of light rays striking the macular in age related Macular Degeneration. Finally, the formation of a superficial deep blue-black ring on the cornel surface can have therapeutic benefit in the treatment of presbyopia.

OTHER EMBODIMENTS

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention herein. Such equivalents are intended to be encompassed in the scope of the present invention.

All references, including patents, publications, and patent applications, mentioned in this specification are herein incorporated by reference in the same extent as if each independent publication, patent or patent application was specifically and individually indicated to be incorporated by reference.

We claim:

1. A method for localized staining of an intact tissue surface comprising the steps of:
   positioning a staging device on said intact tissue surface so that the staging device defines a desired treatment area;
   deprotonating ϵ-amino groups of lysine residues on exposed proteins of a desired treatment area of said intact tissue surface, without an resulting softening of said intact tissue surface;
   applying a chemical dye to said desired treatment area, wherein said chemical dye reacts with said tissue resulting in covalent bonding of said chemical dye to the deprotonated ϵ-amino groups of lysine residues on said exposed proteins; and
   rinsing the desired treatment area to remove unreacted chemical dye, said reacted chemical dye remaining in the desired treatment area to create a dark stain on said intact tissue surface.

2. The method of claim 1 wherein said step of deprotonating comprises the step of applying a slightly alkaline buffer solution to the desired treatment area to increase the pH thereof.

3. The method of claim 1 wherein said chemical dye comprises an acylation reagent.

4. The method of claim 3 wherein said acylation reagent comprises a sulfonic acid reagent.

5. The method of claim 3 wherein said acylation agent is selected from the group consisting of: sulfonic acids, anhydrides, sulfonyl chlorides, and acid chlorides.

6. The method of claim 1 wherein said intact tissue surface comprises corneal tissue and said desired treatment area is selected for the correction of an optical aberration.

7. The method of claim 6 wherein said desired treatment area comprises a spot.

8. The method of claim 6 wherein said desired treatment area comprises an annular ring.

9. A method for localized staining of an intact corneal tissue surface comprising the steps of:
   defining a desired treatment area of said intact corneal tissue surface, wherein said desired treatment area is selected for the correction of an optical abberation;
   applying a chemical dye to said desired treatment area, wherein said chemical dye reacts with said tissue resulting in bonding of said chemical dye to exposed proteins of said tissue; and
   rinsing the desired treatment area to remove unreacted chemical dye, said reacted chemical dye remaining in the desired treatment area to create a dark stain on said intact tissue surface.

10. The method of claim 9 wherein said step of applying said chemical dye includes the steps of:
    deprotonating ϵ-amino groups of lysine residues on exposed proteins of a desired treatment area of said intact tissue surface, without any resulting softening of said intact tissue surface; and
    applying a chemical dye to said desired treatment area, wherein said chemical dye reacts with said tissue resulting in covalent bonding of said chemical dye to the deprotonated ϵ-amino groups of lysine residues on said exposed proteins.

11. The method of claim 10 wherein said chemical dye comprises an acylation reagent.

12. The method of claim 11 wherein said acylation reagent comprises a sulfonic acid reagent.

13. The method of claim 11 wherein said acylation agent is selected from the group consisting of: sulfonic acids, anhydrides, sulfonyl chlorides, and acid chlorides.

14. The method of claim 9 wherein said desired treatment area comprises a spot.

15. The method of claim 9 wherein said desired treatment area comprises an annular ring.

16. The method of claim 9 wherein said step of applying said chemical dye comprises the steps of:
    providing an absorbent material having an application surface that is shaped in the configuration of said desired treatment area;
    pre-dosing said absorbent material with a therapeutically effective amount of said chemical dye; and
    positioning said absorbent material in aligned contact with said desired treatment area; and
    wetting the absorbent material to release and deliver the pre-dosed chemical dye to the desired treatment area of the intact corneal tissue surface.

* * * * *